(12) United States Patent
Boucher et al.

(10) Patent No.: US 9,408,988 B2
(45) Date of Patent: *Aug. 9, 2016

(54) INHALED HYPERTONIC SALINE DELIVERED BY A HEATED NASAL CANNULA

(71) Applicant: Parion Sciences, Inc., Durham, NC (US)

(72) Inventors: Richard C. Boucher, Chapel Hill, NC (US); Michael Ross Johnson, Chapel Hill, NC (US)

(73) Assignee: Parion Sciences, Inc., Durham, NC (US)

( * ) Notice: Subject to any disclaimer, the term of this patent is extended or adjusted under 35 U.S.C. 154(b) by 330 days.

This patent is subject to a terminal disclaimer.

(21) Appl. No.: 14/047,281

(22) Filed: Oct. 7, 2013

(65) Prior Publication Data

US 2014/0096765 A1    Apr. 10, 2014

Related U.S. Application Data

(63) Continuation of application No. 12/249,175, filed on Oct. 10, 2008, now Pat. No. 8,551,534.

(60) Provisional application No. 60/978,887, filed on Oct. 10, 2007.

(51) Int. Cl.
| | | |
|---|---|---|
| *A61K 33/00* | (2006.01) | |
| *A61M 15/08* | (2006.01) | |
| *A61M 11/02* | (2006.01) | |
| *A61M 16/06* | (2006.01) | |
| *A61M 11/00* | (2006.01) | |

(Continued)

(52) U.S. Cl.
CPC ............ *A61M 15/08* (2013.01); *A61M 11/001* (2014.02); *A61M 11/02* (2013.01); *A61M 16/0666* (2013.01); *A61M 16/0875* (2013.01); *A61M 16/1075* (2013.01); *A61M 16/1095* (2014.02); *A61M 16/18* (2013.01); *A61M 16/14* (2013.01)

(58) Field of Classification Search
None
See application file for complete search history.

(56) References Cited

U.S. PATENT DOCUMENTS

| | | |
|---|---|---|
| 3,313,813 A | 4/1967 | Cragoe, Jr. |
| 4,159,803 A | 7/1979 | Cameto et al. |

(Continued)

FOREIGN PATENT DOCUMENTS

| | | |
|---|---|---|
| EP | 1481702 | 12/2004 |
| EP | 1715909 | 11/2006 |

(Continued)

OTHER PUBLICATIONS

Supplementary Partial European Search Report for European Application No. 08837710.6, mailed Jun. 6, 2014, 8 pages.

(Continued)

*Primary Examiner* — Robert A Wax
*Assistant Examiner* — Melissa Mercier

(57) ABSTRACT

The invention described herein is directed to method of treating chronic obstructive pulmonary disease, comprising administering an effective amount of an osmolyte by at least one nasal cannula to a subject in need thereof. Also provided is a nasal cannula system for delivering an osmolyte, comprising a nebulizer and tubing having two ends, where the first end of the tubing is connected to the nebulizer and the second end of the tubing is tapered to fit in the nostril of a subject.

25 Claims, 1 Drawing Sheet

(51) Int. Cl.
  *A61M 16/10* (2006.01)
  *A61M 16/08* (2006.01)
  *A61M 16/18* (2006.01)
  *A61M 16/14* (2006.01)

(56) References Cited

U.S. PATENT DOCUMENTS

| | | | |
|---|---|---|---|
| 4,268,460 A | 5/1981 | Boiarski et al. |
| 4,312,860 A | 1/1982 | Clements |
| 4,479,932 A | 10/1984 | Bodor |
| 4,501,729 A | 2/1985 | Boucher et al. |
| 4,540,564 A | 9/1985 | Bodor |
| 5,002,048 A | 3/1991 | Makiej, Jr. |
| 5,007,419 A | 4/1991 | Weinstein et al. |
| 5,100,806 A | 3/1992 | Macri |
| 5,292,498 A | 3/1994 | Boucher, Jr. |
| 5,388,574 A | 2/1995 | Ingebrethsen |
| 5,437,267 A | 8/1995 | Weinstein et al. |
| 5,483,953 A | 1/1996 | Cooper |
| 5,533,506 A | 7/1996 | Wood |
| 5,614,216 A | 3/1997 | Janoff |
| 5,656,256 A | 8/1997 | Boucher et al. |
| 5,687,715 A | 11/1997 | Landis et al. |
| 5,817,028 A | 10/1998 | Anderson |
| 5,876,970 A | 3/1999 | Benson et al. |
| 6,015,828 A | 1/2000 | Cuppoletti |
| 6,159,969 A | 12/2000 | Yano et al. |
| 6,214,536 B1 | 4/2001 | Boucher, Jr. |
| 6,223,745 B1 | 5/2001 | Hammarlund et al. |
| 6,264,975 B1 | 7/2001 | Boucher, Jr. |
| 6,348,589 B1 | 2/2002 | Pendergast et al. |
| 6,387,886 B1 | 5/2002 | Montgomery et al. |
| 6,457,472 B1 | 10/2002 | Schwartz et al. |
| 6,527,151 B1 | 3/2003 | Pavkov et al. |
| 6,530,370 B1 | 3/2003 | Heinonen |
| 6,550,476 B1 | 4/2003 | Ryder |
| 6,630,121 B1 | 10/2003 | Sievers et al. |
| 6,818,629 B2 | 11/2004 | Peterson et al. |
| 6,858,614 B2 | 2/2005 | Johnson |
| 6,858,615 B2 | 2/2005 | Johnson |
| 6,903,105 B2 | 6/2005 | Johnson |
| 6,926,911 B1 | 8/2005 | Boucher, Jr. |
| 6,977,246 B2 | 12/2005 | Pendergast et al. |
| 6,995,160 B2 | 2/2006 | Johnson |
| 7,026,325 B2 | 4/2006 | Johnson |
| 7,030,117 B2 | 4/2006 | Johnson |
| 7,064,129 B2 | 6/2006 | Johnson et al. |
| 7,186,833 B2 | 3/2007 | Johnson |
| 7,189,719 B2 | 3/2007 | Johnson |
| 7,192,958 B2 | 3/2007 | Johnson |
| 7,192,959 B2 | 3/2007 | Johnson |
| 7,192,960 B2 | 3/2007 | Johnson |
| 7,201,167 B2 | 4/2007 | Fink et al. |
| 7,223,744 B2 | 5/2007 | Yerxa et al. |
| 7,241,766 B2 | 7/2007 | Johnson |
| 7,247,636 B2 | 7/2007 | Johnson |
| 7,247,637 B2 | 7/2007 | Johnson et al. |
| 7,253,295 B2 | 8/2007 | Ueno et al. |
| 7,267,121 B2 | 9/2007 | Ivri |
| 7,314,046 B2 | 1/2008 | Schroeder et al. |
| 7,317,013 B2 | 1/2008 | Johnson |
| 7,332,496 B2 | 2/2008 | Johnson |
| 7,345,044 B2 | 3/2008 | Johnson |
| 7,345,051 B2 | 3/2008 | Zhou et al. |
| 7,368,447 B2 | 5/2008 | Johnson et al. |
| 7,368,450 B2 | 5/2008 | Johnson |
| 7,368,451 B2 | 5/2008 | Johnson et al. |
| 7,375,107 B2 | 5/2008 | Johnson |
| 7,388,013 B2 | 6/2008 | Johnson et al. |
| 7,399,766 B2 | 7/2008 | Johnson |
| 7,405,233 B2 | 7/2008 | Wilde et al. |
| 7,410,968 B2 | 8/2008 | Johnson et al. |
| 7,482,024 B2 | 1/2009 | Kuo et al. |
| 7,499,570 B2 | 3/2009 | Zoghlami et al. |
| 7,517,865 B2 | 4/2009 | Meyers |
| 7,531,525 B2 | 5/2009 | Yerxa et al. |
| 7,537,009 B2 | 5/2009 | Hale et al. |
| 7,553,855 B2 | 6/2009 | Young et al. |
| 7,607,436 B2 | 10/2009 | Smaldone et al. |
| 7,645,789 B2 | 1/2010 | Hadida Ruah et al. |
| 7,745,442 B2 | 6/2010 | Johnson et al. |
| 7,772,259 B2 | 8/2010 | Karp et al. |
| 7,807,834 B2 | 10/2010 | Johnson |
| 7,820,678 B2 | 10/2010 | Johnson |
| 7,842,697 B2 | 11/2010 | Johnson |
| 7,868,010 B2 | 1/2011 | Johnson et al. |
| 7,875,619 B2 | 1/2011 | Johnson |
| 7,897,577 B2 | 3/2011 | Johansson et al. |
| 7,900,625 B2 | 3/2011 | Kleinstreuer et al. |
| 7,905,229 B2 | 3/2011 | Giroux et al. |
| 7,956,059 B2 | 6/2011 | Johnson |
| 7,981,898 B2 | 7/2011 | Johnson et al. |
| 8,001,963 B2 | 8/2011 | Giroux |
| 8,008,494 B2 | 8/2011 | Johnson |
| 8,022,210 B2 | 9/2011 | Johnson |
| 8,058,278 B2 | 11/2011 | Johnson et al. |
| 8,061,352 B2 | 11/2011 | Grychowski et al. |
| 8,105,572 B2 | 1/2012 | Condos et al. |
| 8,124,607 B2 | 2/2012 | Johnson |
| 8,143,256 B2 | 3/2012 | Johnson |
| 8,163,758 B2 | 4/2012 | Johnson et al. |
| 8,198,286 B2 | 6/2012 | Johnson |
| 8,288,391 B2 | 10/2012 | Johnson |
| 8,314,105 B2 | 11/2012 | Johnson et al. |
| 8,324,218 B2 | 12/2012 | Johnson |
| 8,551,534 B2 | 10/2013 | Boucher et al. |
| 8,778,383 B2 | 7/2014 | Boucher et al. |
| 8,945,605 B2 | 2/2015 | Boucher et al. |
| 2002/0129812 A1 | 9/2002 | Litherland et al. |
| 2003/0091512 A1 | 5/2003 | Adjei et al. |
| 2003/0171332 A1 | 9/2003 | Abraham et al. |
| 2003/0209246 A1* | 11/2003 | Schroeder ......... A61M 16/0808  128/204.17 |
| 2004/0192786 A1 | 9/2004 | Welsh et al. |
| 2004/0244804 A1 | 12/2004 | Olsen et al. |
| 2005/0080093 A1 | 4/2005 | Johnson et al. |
| 2005/0090505 A1 | 4/2005 | Johnson et al. |
| 2005/0229926 A1 | 10/2005 | Fink et al. |
| 2005/0229928 A1 | 10/2005 | Ivri et al. |
| 2005/0229929 A1 | 10/2005 | Ivri |
| 2006/0078506 A1 | 4/2006 | Niven et al. |
| 2006/0142306 A1 | 6/2006 | Johnson |
| 2006/0142581 A1 | 6/2006 | Johnson |
| 2006/0144399 A1 | 7/2006 | Davidowski et al. |
| 2007/0032509 A1 | 2/2007 | Johnson et al. |
| 2007/0157931 A1 | 7/2007 | Parker et al. |
| 2007/0202051 A1 | 8/2007 | Schuschnig |
| 2007/0265280 A1 | 11/2007 | Johnson |
| 2007/0267010 A1 | 11/2007 | Fink et al. |
| 2008/0000473 A1 | 1/2008 | Stephenson et al. |
| 2008/0035141 A1 | 2/2008 | Warner et al. |
| 2008/0066741 A1 | 3/2008 | LeMahieu et al. |
| 2008/0072899 A1 | 3/2008 | Niland et al. |
| 2008/0076782 A1 | 3/2008 | Johnson |
| 2008/0078382 A1 | 4/2008 | LeMahieu et al. |
| 2008/0090841 A1 | 4/2008 | Johnson et al. |
| 2008/0096896 A1 | 4/2008 | Johnson |
| 2008/0103148 A1 | 5/2008 | Johnson |
| 2008/0167466 A1 | 7/2008 | Johnson et al. |
| 2008/0171879 A1 | 7/2008 | Johnson |
| 2008/0171880 A1 | 7/2008 | Johnson et al. |
| 2008/0176863 A1 | 7/2008 | Johnson et al. |
| 2008/0177072 A1 | 7/2008 | Johnson |
| 2008/0199410 A1 | 8/2008 | Johnson et al. |
| 2008/0200476 A1 | 8/2008 | Johnson |
| 2008/0223375 A1 | 9/2008 | Cortez et al. |
| 2008/0249109 A1 | 10/2008 | Johnson et al. |
| 2008/0264415 A1 | 10/2008 | Eason et al. |
| 2008/0293740 A1 | 11/2008 | Johnson et al. |
| 2009/0018144 A1 | 1/2009 | Johnson et al. |
| 2009/0025713 A1 | 1/2009 | Keller et al. |
| 2009/0062308 A1 | 3/2009 | Johnson |
| 2009/0104272 A1 | 4/2009 | Boucher et al. |
| 2009/0203752 A1 | 8/2009 | Campbell et al. |

(56) References Cited

U.S. PATENT DOCUMENTS

| | | |
|---|---|---|
| 2009/0221597 A1 | 9/2009 | Ruah et al. |
| 2009/0246137 A1 | 10/2009 | Hadida Ruah et al. |
| 2009/0246820 A1 | 10/2009 | Singh et al. |
| 2009/0247458 A1 | 10/2009 | Watson et al. |
| 2009/0253714 A1 | 10/2009 | Johnson et al. |
| 2009/0253736 A1 | 10/2009 | Hadida Ruah et al. |
| 2009/0263495 A1 | 10/2009 | Watson et al. |
| 2009/0288658 A1 | 11/2009 | Charan et al. |
| 2009/0306009 A1 | 12/2009 | Rosenmeier |
| 2009/0324724 A1 | 12/2009 | Johnson |
| 2010/0074881 A1 | 3/2010 | Boucher et al. |
| 2010/0081957 A1 | 4/2010 | Hyde et al. |
| 2010/0089395 A1 | 4/2010 | Power et al. |
| 2010/0092402 A1 | 4/2010 | Hall et al. |
| 2010/0130547 A1 | 5/2010 | Zhang et al. |
| 2010/0168094 A1 | 7/2010 | Binch et al. |
| 2010/0184739 A1 | 7/2010 | Sheth et al. |
| 2010/0209357 A1 | 8/2010 | Levitt |
| 2010/0209540 A1 | 8/2010 | Warner et al. |
| 2010/0215588 A1 | 8/2010 | Skaliter |
| 2010/0227888 A1 | 9/2010 | Ruah et al. |
| 2010/0258114 A1 | 10/2010 | Cortez et al. |
| 2010/0316628 A1 | 12/2010 | Breton et al. |
| 2011/0008366 A1 | 1/2011 | Wight et al. |
| 2011/0053831 A1 | 3/2011 | Milech et al. |
| 2011/0056492 A1 | 3/2011 | Longest et al. |
| 2011/0104255 A1 | 5/2011 | Niitsu et al. |
| 2011/0120457 A1 | 5/2011 | Dhuper et al. |
| 2011/0171141 A1 | 7/2011 | Kellerman et al. |
| 2011/0195973 A1 | 8/2011 | Johnson |
| 2011/0214673 A1 | 9/2011 | Masionis |
| 2012/0107414 A1 | 5/2012 | Lipp et al. |
| 2012/0125332 A1 | 5/2012 | Niland et al. |
| 2012/0192863 A1 | 8/2012 | Power et al. |
| 2012/0251594 A1 | 10/2012 | Longest et al. |
| 2013/0074842 A1 | 3/2013 | Boucher |
| 2014/0109899 A1 | 4/2014 | Boucher et al. |
| 2014/0158127 A1 | 6/2014 | Boucher et al. |
| 2015/0101597 A1 | 4/2015 | Boucher et al. |
| 2015/0150803 A1 | 6/2015 | Boucher et al. |

FOREIGN PATENT DOCUMENTS

| | | |
|---|---|---|
| WO | WO 96/20748 | 7/1996 |
| WO | WO 2006/072231 | 7/2006 |
| WO | WO 2009/049159 | 4/2009 |
| WO | WO 2009/134524 | 11/2009 |

OTHER PUBLICATIONS

Supplementary European Search Report for European Application No. 12797275.0, mailed Oct. 10, 2014, 7 pages.
Office Action for U.S. Appl. No. 13/831,268, mailed Mar. 25, 2014, 8 pages.
International Search Report and Written Opinion for International Application No. PCT/US2013/073708, mailed Mar. 28, 2014, 15 pages.
U.S. Appl. No. 60/909,802, filed Apr. 3, 2007, Johnson et al.
Office Action for Australian Application No. 2008310734, dated Dec. 14, 2012, 3 pages.
Office Action for U.S. Appl. No. 12/249,175, mailed Nov. 20, 2012, 9 pages.
Office Action for U.S. Appl. No. 12/249,175, mailed Apr. 14, 2011, 12 pages.
Office Action for U.S. Appl. No. 12/249,175, mailed Oct. 7, 2010, 11 pages.
International Search Report and Written Opinion for International Application No. PCT/US2008/079519, mailed Dec. 16, 2008.
International Preliminary Report on Patentability for International Application No. PCT/US2008/079519, dated Apr. 13, 2010, 6 pages.
Office Action for U.S. Appl. No. 13/491,275, mailed Sep. 12, 2013.
International Search Report for International Application No. PCT/US2013/038368, mailed Sep. 16, 2013.
Aerogen Limited, AeronebPro Micropump Nebulizer, Instruction Manual, 56 pages (2011).
Bhashyam, A. et aL, "Aerosol delivery through nasal cannulas: An in vitro study," Journal of Aerosol Medicine, 21(2):1-7 (2008).
Donaldson, S. et al., "Mucus clearance and lung function in cystic fibrosis with hypertonic saline," The New England Journal of Medicine, 354(3):241-250 (2006).
Elkins, M. et al., "A controlled trial of long-term inhaled hypertonic saline in patients with cystic fibrosis," The New England Journal of Medicine, 354(3):229-240 (2006).
Heyder, J. et al., "Deposition of particles in the human respiratory tract in the size range of 0.005-15 μm," J Aerosol. Sci., 17(5):811-825 (1986).
Longest, P. W. et al., "High-efficiency generation and delivery of aerosols through nasal cannula during noninvasive ventilation," Journal of Aerosol Medicine and Pulmonary Drug Delivery, 26(5):266-279 (2013).
O'Callaghan, C. et al., "The science of nebulised drug delivery," Thorax, 52(2):S31-S44 (1997).
PARI Reusable Nebulizer Configurations, PARI Respiratory Equipment, Inc., Brochure—LC Nebulizers.
Randell, S. H. et al., "Effective mucos clearance is essential for respiratory health," Am. J. Respir. Cell. Mol. Biol., 35(1):20-28 (2006).
Reusable Nebulizers [online] Jun. 2010, [retrieved on Jan. 6, 2011], retrieved from http://www.pari.com/downloads/product-brochures/PARI_LC_Nebs_Brochure_Rev-C_EN.pdf.
Westerman et al., "Aerosolization of Tobramycin (TOBI®) with the PARI LC PLUS® Reusable Nebulizer: Which Compressor to Use? Comparison of the CR60® to the PortaNeb® Compressor," Journal of Aerosol Medicine and Pulmonary Drug Delivery, 21(3):269-280 (2008).
Office Action for Canadian Application No. 2,702,094, dated Dec. 10, 2014.
Office Action for Canadian Application No. 2,702,094, dated Jul. 20, 2015.
Office Action for Canadian Application No. 2,702,094, dated Mar. 31, 2016.

* cited by examiner

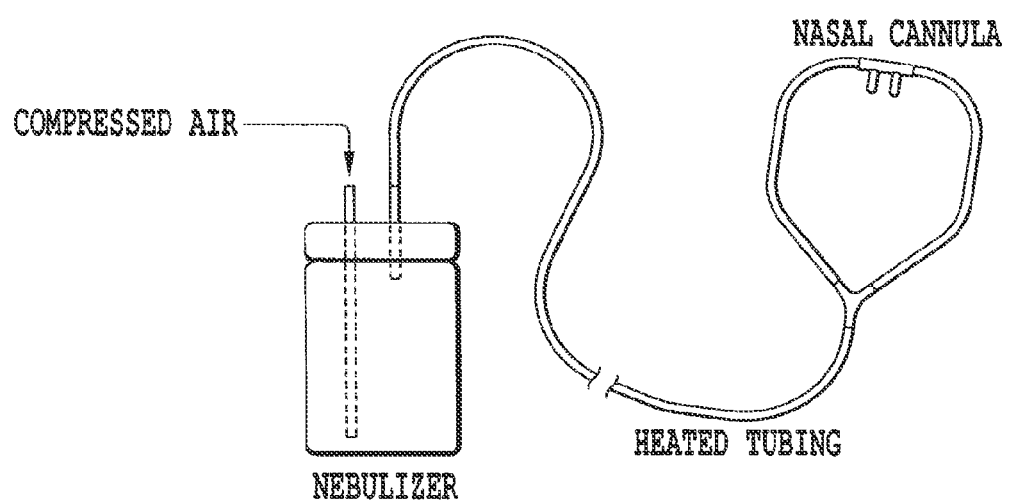

INHALED HYPERTONIC SALINE DELIVERED BY A HEATED NASAL CANNULA

CONTINUING APPLICATION DATA

This application is a continuation of U.S. application Ser. No. 12/249,175, filed on Oct. 10, 2008, which claims priority to and the benefit of U.S. provisional application Ser. No. 60/978,887, filed on Oct. 10, 2007, both of which are incorporated herein by reference in their entirety.

BACKGROUND OF THE INVENTION

1. Field of the Invention

The present invention relates to the aerosolized delivery of hypertonic saline (HS) and other osmolytes to provide overnight nasal hydration to patients with all forms of chronic obstructive pulmonary disease (COPD) over a long period of time. The present invention also relates to a device and apparatus with a sufficient reservoir to accomplish the same.

2. Description of the Background

The mucosal surfaces at the interface between the environment and the body have evolved a number of "innate defenses", i.e., protective mechanisms. A principal form of such innate defense is to cleanse these surfaces with liquid. Typically, the quantity of the liquid layer on a mucosal surface reflects the balance between epithelial liquid secretion, often reflecting active anion ($Cl^-$ and/or $HCO^3$) secretion coupled with water (and a cation counter-ion), and epithelial liquid absorption, often reflecting active $Na^+$ absorption, coupled with water and counter anion ($Cl^-$ and/or $HCO^3$). Many diseases of mucosal surfaces are caused by too little protective liquid on those mucosal surfaces created by an imbalance between secretion (too little) and absorption (relatively too much). The defective salt transport processes that characterize these mucosal dysfunctions reside in the epithelial layer of the mucosal surface.

One approach to replenish the protective liquid layer on mucosal surfaces is to "re-balance" the system by blocking $Na^+$ channel and liquid absorption. The epithelial protein that mediates the rate-limiting step of $Na^+$ and liquid absorption is the epithelial $Na^+$ channel (ENaC). ENaC is positioned on the apical surface of the epithelium, i.e. the mucosal surface-environmental interface. Therefore, to inhibit ENaC mediated $Na^+$ and liquid absorption, an ENaC blocker of the amiloride class (which blocks from the extracellular domain of ENaC) must be delivered to the mucosal surface and, importantly, be maintained at this site, to achieve therapeutic utility. The present invention describes diseases characterized by too little liquid on mucosal surfaces and "topical" sodium channel blockers designed to exhibit the increased potency, reduced mucosal absorbtion, and slow dissociation ("unbinding" or detachment) from ENaC required for therapy of these diseases.

Chronic obstructive pulmonary diseases are characterized by dehydration of airway surfaces and the retention of mucous secretions in the lungs. Examples of such diseases include cystic fibrosis, chronic bronchitis, and primary or secondary ciliary dyskinesia. Such diseases affect approximately 15 million patients in the United States, and are the sixth leading cause of death. Other airway or pulmonary diseases characterized by the accumulation of retained mucous secretions include sinusitis (an inflammation of the paranasal sinuses associated with upper respiratory infection) and pneumonia.

U.S. Pat. No. 5,817,028 to Anderson describes a method for the provocation of air passage narrowing (for evaluating susceptibility to asthma) and/or the induction of sputum in subjects via the inhalation of mannitol. It is suggested that the same technique can be used to induce sputum and promote mucociliary clearance. Substances suggested include osmolytes such as sodium chloride, potassium chloride, mannitol and dextrose.

Chronic bronchitis (CB), including the most common lethal genetic form of chronic bronchitis, cystic fibrosis (CF), a disease that reflects the body's failure to clear mucus normally from the lungs, which ultimately produces chronic airways infection. In the normal lung, the primary defense against chronic intrapulmonary airways infection (chronic bronchitis) is mediated by the continuous clearance of mucus from bronchial airway surfaces. This function in health effectively removes from the lung potentially noxious toxins and pathogens. Recent data indicate that the initiating problem, i.e., the "basic defect," in both CB and CF is the failure to clear mucus from airway surfaces. The failure to clear mucus reflects dehydration of airway surfaces that reflects an imbalance between the amount of liquid and mucin on airway surfaces. This "airway surface liquid" (ASL) is primarily composed of salt and water in proportions similar to plasma (i.e., isotonic). Mucin macromolecules organize into a well defined "mucus layer" which normally traps inhaled bacteria and is transported out of the lung via the actions of cilia which beat in a watery, low viscosity solution termed the "periciliary liquid" (PCL). In the disease state, there is an imbalance in the quantities of mucins (too much) and ASL (too little) on airway surfaces that produces airway surface dehydration. This dehydration leads to mucus concentration, reduction in the lubricant activity of the PCL, and a failure to clear mucus via ciliary activity to the mouth. The reduction in mechanical clearance of mucus from the lung leads to chronic airways inflammation and bacterial colonization of mucus adherent to airway surfaces. It is the chronic retention of bacteria, the failure of local antimicrobial substances to kill mucus-entrapped bacteria on a chronic basis, and the consequent chronic inflammatory responses of the body to this type of surface infection, that lead to the destruction of the lung in CB and CF.

The current afflicted population in the U.S. is 12,000,000 patients with the acquired (primarily from cigarette smoke exposure) form of chronic bronchitis and approximately 30,000 patients with the genetic form, cystic fibrosis. Approximately equal numbers of both populations are present in Europe. In Asia, there is little CF but the incidence of CB is high and, like the rest of the world, is increasing.

There is currently a large, unmet medical need for products that specifically treat CB and CF at the level of the basic defect that cause these diseases. The current therapies for chronic bronchitis and cystic fibrosis focus on treating the symptoms and/or the late effects of these diseases. Thus, for chronic bronchitis, fl-agonists, inhaled steroids, anti-cholinergic agents, and oral theophyllines and phosphodiesterase inhibitors are all in development. However, none of these drugs treat effectively the fundamental problem of the failure to clear mucus from the lung. Similarly, in cystic fibrosis, the same spectrum of pharmacologic agents is used. These strategies have been complemented by more recent strategies designed to clear the CF lung of the DNA ("Pulmozyme"; Genentech) that has been deposited in the lung by neutrophils that have futilely attempted to kill the bacteria that grow in adherent mucus masses and through the use of inhaled antibiotics ("TOBI") designed to augment the lungs' own killing mechanisms to rid the adherent mucus plaques of bacteria. A general principle of the body is that if the initiating lesion is not treated, in this case mucus retention/obstruction, bacterial infections became chronic and increasingly refractory to antimicrobial therapy. Thus, a major unmet therapeutic need for both CB and CF lung diseases is an effective means of rehydrating airway mucus (i.e., restoring/expanding the volume of the ASL) and promoting its clearance, with bacteria, from the lung.

The inhalation of osmolytes/osmolyte solutions, such as hypertonic saline (3-12% preferred embodiment 7%) has been demonstrated to be a safe and effective treatment for individuals with cystic fibrosis. Inhaled hypertonic saline improves mucus hydration and clearance, and is associated with improvements in lung function, as well as, a reduction in the number of infectious exacerbations over one year (Donaldson et al. N. Engl. J. Med. 354, 3, Jan. 19, 2006, pp. 241-250) and Elkins et al. (N. Engl. J. Med. 354, 3, Jan. 19, 2006, pp. 229-240).

A limitation of inhaled osmolytes to increase mucosal hydration is the durability of the therapeutic effect of the osmolytes. In cell based assays, the ability of the mucosal epithelium to efficiently absorb fluid results in the reversal of osmolyte-induced surface hydration. The relatively short therapeutic benefit of inhaled osmolytes can be overcome by increasing the number of treatments per day. For example, Donaldson et al. (*N. Engl. J. Med.* 354, 3, Jan. 19, 2006, pp. 241-250) showed inhaling 7% HS four times daily increased FEV1 by two fold greater than observed by Elkins et al. (*N. Engl. J. Med.* 354, 3, Jan. 19, 2006, pp. 229-240) in CF patients inhaling 7% HS twice daily. However, increasing the dosing frequency of hypertonic saline or other osmolytes is inconvenient for subjects in need thereof, requiring hours of time taking medications during the day.

Clearly, what are needed are treatments that are more effective at restoring the clearance of mucus from the lungs of patients with CB/CF. The value of these new therapies will be reflected in improvements in the quality and duration of life for both the CF and the CB populations.

In U.S. patent application Ser. No. 11/851,803, R. C. Boucher and M. R. Johnson describe a method to extend the duration of osmolyte therapy by co-administering a potent sodium channel blockers. The inhibition of epithelial sodium transport prevents the reabsorption of HS osmolytes, and thereby, slows mucosal fluid absorption and extends the duration of mucosal hydration. The present invention describes an alternative approach to improving both the therapeutic benefit and convenience to the of inhaled osmolyte treatments.

SUMMARY OF THE INVENTION

The present invention is designed to improve the dosing of an osmolyte (e.g., HS) delivered to the lungs of subjects in need of airway surface rehydration by delivering the osmolyte to the lung via nasal cannulae. The present invention will permit subjects to be treated for long periods of time (e.g., hours) while sleeping or performing daily activities.

Thus, an object of the present invention is a method of treating chronic obstructive pulmonary disease by administering an effective amount of an aerosolized osmolyte to a subject in need thereof with a nebulizer connected to a nasal cannula.

Another object of the present invention is a nasal cannula system for delivering an osmolyte, comprising:
a nebulizer and
tubing, where one end of the tubing is connected to the nebulizer and another end of the tubing is tapered to fit in the nostril of a subject.

A more complete appreciation of the invention and many of the attendant advantages thereof will be readily obtained as the same becomes better understood by reference to the following FIGURE and detailed description.

BRIEF DESCRIPTION OF THE FIGURES

FIG. 1: Example of a nebulizer device capable of delivering osmolytes for extended periods of time. The diagram shows a standard large volume nebulizer (with >100 ml capacity) connected to a nasal cannula with heated tubing.

DETAILED DESCRIPTION OF THE INVENTION

Osmolytes are well-known therapeutics in the field of respiratory therapeutics. These agents are molecules or compounds that are osmotically active (i.e., are "osmolytes"). "Osmotically active" compounds of the present invention are membrane-impermeable (i.e., essentially non-absorbable) on the airway or pulmonary epithelial surface. The terms "airway surface" and "pulmonary surface," as used herein, include pulmonary airway surfaces such as the bronchi and bronchioles, alveolar surfaces, and nasal and sinus surfaces. Active compounds of the present invention may be ionic osmolytes (i.e., salts), or may be non-ionic osmolytes (i.e., sugars, sugar alcohols, and organic osmolytes). It is specifically intended that both racemic forms of the active compounds that are racemic in nature are included in the group of active compounds that are useful in the present invention. It is to be noted that all racemates, enantiomers, diastereomers, tautomers, polymorphs and pseudopolymorphs and racemic mixtures of the osmotically active compounds are embraced by the present invention.

Active osmolytes useful in the present invention that are ionic osmolytes include any salt of a pharmaceutically acceptable anion and a pharmaceutically acceptable cation. Preferably, either (or both) of the anion and cation are non-absorbable (i.e., osmotically active and not subject to rapid active transport) in relation to the airway surfaces to which they are administered. Such compounds include but are not limited to anions and cations that are contained in FDA approved commercially marketed salts, see, e.g., *Remington: The Science and Practice of Pharmacy*, Vol. 11, pg. 1457 (19$^{th}$ Ed. 1995), incorporated herein by reference, and can be used in any combination including their conventional combinations.

Pharmaceutically acceptable osmotically active anions that can be used to carry out the present invention include, but are not limited to, acetate, benzenesulfonate, benzoate, bicarbonate, bitartrate, bromide, calcium edetate, camsylate (camphorsulfonate), carbonate, chloride, citrate, dihydrochloride, edetate, edisylate (1,2-ethanedisulfonate), estolate (lauryl sulfate), esylate (1,2-ethanedisulfonate), fumarate, gluceptate, gluconate, glutamate, glycollylarsanilate (p-glycollamidophenylarsonate), hexylresorcinate, hydrabamine (N,N'-Di(dehydroabietyl)ethylenediamine), hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, nitrate, nitrite, pamoate (embonate), pantothenate, phosphate or diphosphate, polygalacturonate, salicylate, stearate, subacetate, succinate, sulfate, tannate, tartrate, teoclate (8-chlorotheophyllinate), triethiodide, bicarbonate, etc. Particularly preferred anions include chloride sulfate, nitrate, gluconate, iodide, bicarbonate, bromide, and phosphate.

Pharmaceutically acceptable cations that can be used to carry out the present invention include, but are not limited to, organic cations such as benzathine (N,N'-dibenzylethylenediamine), chloroprocaine, choline, diethanolamine, ethylenediamine, meglumine (N-methyl D-glucamine), procaine, D-lysine, L-lysine, D-arginine, L-arginine, triethylammonium, N-methyl D-glycerol, and the like. Particularly preferred organic cations are 3-carbon, 4-carbon, 5-carbon and 6-carbon organic cations. Metallic cations useful in the practice of the present invention include but are not limited to aluminum, calcium, lithium, magnesium, potassium, sodium, zinc, iron, ammonium, and the like. Particularly preferred cations include sodium, potassium, choline, lithium, meglumine, D-lysine, ammonium, magnesium, and calcium.

Specific examples of osmotically active salts that may be used with the sodium channel blockers described herein to carry out the present invention include, but are not limited to, sodium chloride, potassium chloride, choline chloride, choline iodide, lithium chloride, meglumine chloride, L-lysine chloride, D-lysine chloride, ammonium chloride, potassium sulfate, potassium nitrate, potassium gluconate, potassium iodide, ferric chloride, ferrous chloride, potassium bromide, etc. Either a single salt or a combination of different osmotically active salts may be used to carry out the present invention. Combinations of different salts are preferred. When different salts are used, one of the anion or cation may be the same among the differing salts.

Osmotically active compounds of the present invention also include non-ionic osmolytes such as sugars, sugar-alcohols, and organic osmolytes. Sugars and sugar-alcohols useful in the practice of the present invention include but are not limited to 3-carbon sugars (e.g., glycerol, dihydroxyacetone); 4-carbon sugars (e.g., both the D and L forms of erythrose, threose, and erythrulose); 5-carbon sugars (e.g., both the D and L forms of ribose, arabinose, xylose, lyxose, psicose, fructose, sorbose, and tagatose); and 6-carbon sugars (e.g., both the D- and L-forms of altose, allose, glucose, mannose, gulose, idose, galactose, and talose, and the D- and L-forms of allo-heptulose, allo-hepulose, gluco-heptulose, manno-heptulose, gulo-heptulose, ido-heptulose, galacto-heptulose, talo-heptulose). Additional sugars useful in the practice of the present invention include raffinose, raffinose series oligosaccharides, and stachyose. Both the D- and L-forms of the reduced form of each sugar/sugar alcohol useful in the present invention are also active compounds within the scope of the invention. For example, glucose, when reduced, becomes sorbitol; within the scope of the invention, sorbitol and other reduced forms of sugar/sugar alcohols (e.g., mannitol, dulcitol, arabitol) are accordingly active compounds of the present invention.

Osmotically active compounds of the present invention additionally include the family of non-ionic osmolytes termed "organic osmolytes." The term "organic osmolytes" is generally used to refer to molecules used to control intracellular osmolality in the kidney. See e.g., J. S. Handler et al., Comp. Biochem. Physiol, 117, 301-306 (1997); M. Burg, Am. J. Physiol. 268, F983-F996 (1995), each incorporated herein by reference. Although the inventor does not wish to be bound to any particular theory of the invention, it appears that these organic osmolytes are useful in controlling extracellular volume on the airway/pulmonary surface. Organic osmolytes useful as active compounds in the present invention include but are not limited to three major classes of compounds: polyols (polyhydric alcohols), methylamines, and amino acids. The polyol organic osmolytes considered useful in the practice of this invention include, but are not limited to, inositol, myo-inositol, and sorbitol. The methylamine organic osmolytes useful in the practice of the invention include, but are not limited to, choline, betaine, carnitine (L-, D- and DL-forms), phosphorylcholine, lyso-phosphorylcholine, glycerophosphorylcholine, creatine, and creatine phosphate. The amino acid organic osmolytes of the invention include, but are not limited to, the D- and L-forms of glycine, alanine, glutamine, glutamate, aspartate, proline and taurine. Additional osmolytes useful in the practice of the invention include tihulose and sarcosine. Mammalian organic osmolytes are preferred, with human organic osmolytes being most preferred. However, certain organic osmolytes are of bacterial, yeast, and marine animal origin, and these compounds are also useful active compounds within the scope of the present invention.

Under certain circumstances, an osmolyte precursor may be administered to the subject. Accordingly, these compounds are also useful in the practice of the invention. The term "osmolyte precursor" as used herein refers to a compound which is converted into an osmolyte by a metabolic step, either catabolic or anabolic. The osmolyte precursors of this invention include, but are not limited to, glucose, glucose polymers, glycerol, choline, phosphatidylcholine, lyso-phosphatidylcholine and inorganic phosphates, which are precursors of polyols and methylamines. Precursors of amino acid osmolytes within the scope of this invention include proteins, peptides, and polyamino acids, which are hydrolyzed to yield osmolyte amino acids, and metabolic precursors which can be converted into osmolyte amino acids by a metabolic step such as transamination. For example, a precursor of the amino acid glutamine is poly-L-glutamine, and a precursor of glutamate is poly-L-glutamic acid.

Also included within the scope of this invention are chemically modified osmolytes or osmolyte precursors. Such chemical modifications involve linking to the osmolyte (or precursor) an additional chemical group which alters or enhances the effect of the osmolyte or osmolyte precursor (e.g., inhibits degradation of the osmolyte molecule). Such chemical modifications have been utilized with drugs or prodrugs and are known in the art. (See, for example, U.S. Pat. Nos. 4,479,932 and 4,540,564; Shek, E. et al., J. Med. Chem. 19:113-117 (1976); Bodor, N. et al., J. Pharm. Sci. 67:1045-1050 (1978); Bodor, N. et al., J. Med. Chem. 26:313-318 (1983); Bodor, N. et al., J. Pharm. Sci. 75:29-35 (1986), each incorporated herein by reference.

In general, osmotically active compounds of the present invention (both ionic and non-ionic) that do not promote, or in fact deter or retard bacterial growth, are preferred.

It is an object of the present invention to provide a nebulizer connected to a nasal cannula to deliver aerosolized osmolytes (e.g., HS) to subjects over long time intervals. The nebulizer will have the capacity for a large volume of osmolyte solution (up to 2 liters) and will produce aerosol particles in the respirable range (1-5 microns MMAD) at a rate that will produce good lung deposition and will be continuous, i.e. will not require refilling over long time periods (8-24 hrs). An example of such a nebulizer is the Westmed Heart High Output Nebulizer. A nasal cannula/tubing will be connected to the nebulizer by a tapered fitting. The tubing will have an inner diameter of ~3-5 mm with a length of 2-4 meters. The end of the tubing may end in one or two tapered ends that fit into the nostrils, although face masks are alternatives.

Both nebulizers and nasal cannulas are well-known in the field of respiratory treatment. See Critical Care Medicine (Michael James Murray, American Society of Critical Care Anesthesiologists, Douglas B. Coursin, Ronald G. Pearl, Donald S. Prough), pp. 431 and 439-445. However, commercial nebulizers are generally designed to rapidly delivery therapeutic agents via the mouth or mask. Nasal cannulas are generally used to delivery oxygen (gasses) to the lungs through the nose. Nasal cannulas are preferred for the delivery of gasses as they are comfortable to wear for long periods of time. The adaptation of a nasal cannula on a nebulizer provides a novel means to deliver inhaled osmolytes that offers the following advantages. (1) The nasal cannula/nebulizer device is comfortable and can be worn for extended periods of time. (2) The device can deliver osmolytes for long periods of time, thus, increasing the therapeutic benefit of these treatments.

Due to the narrow diameter of oxygen tubing and nasal cannulas, the output from a nebulizer will lead to the deposition of aerosol on the inner surface of the tubing, leading to the "condensation" and accumulation of fluid droplets. Fluid inside the tubing can occlude the flow of aerosol inside the tubing, as well as, result droplets blowing out the nasal cannula that would "drown" the subject with boluses of liquid.

Several modifications improve the performance of the nasal cannula/nebulizer device to prevent fluid condensation on the inner surface of the tubing and nasal cannula. It is an object of the present invention to heat all the fittings, tubing, and/or the nasal cannula of the device to retard condensation in the tubing. Thus the heated, inner surface coated cannula will ensure that the aerosol generated will be delivered to the nostril as a respirable particle. It is another object of the present invention that the tubing will contain a coating on its inner surface so as to prevent condensation of solution in the lumen. It is anticipated that the subject will use the heated cannulae to receive HS for periods of minutes to daily.

EXAMPLES

The nebulizer system shown in FIG. 1 was run for 80 minutes with 7% hypertonic saline. The build-up of fluid within the oxygen tubing was observed with and without heating the oxygen tubing in a water bath. For this system, the tubing became occluded with water droplets within 23 minutes of continuous nebulizer operation. Externally heating the tubing to 60° C. allow the nebulizer system to run for the full 80 minutes without occlusion from water droplets.

TABLE 1

The effect of heating on fluid condensation within the oxygen tubing.

| Nebulizer/Compressor | Tubing | External Tubing Temperature | Time to Condensation |
|---|---|---|---|
| Pari-LC Star with ProNeb Compressor | Oxygen Tubing with Adult nasal cannula | Ambient | 23 min |
| Pari-LC Star with ProNeb Compressor | Oxygen Tubing with Adult nasal cannula | 60° C. | No significant condensation |

Obviously, numerous modifications and variations of the present invention are possible in light of the above teachings. It is therefore to be understood that within the scope of the appended claims, the invention may be practiced otherwise than as specifically described herein.

The invention claimed is:

1. An apparatus, comprising:
a nasal cannula assembly configured to receive at a first end portion a flow of aerosolized medicament, the nasal cannula assembly configured to convey from the first end portion to a second end portion the flow of aerosolized medicament to deliver the flow of aerosolized medicament transnasally to a subject, the nasal cannula assembly configured to limit accumulation of liquid droplets from the flow of aerosolized medicament.

2. The apparatus of claim 1, wherein the aerosolized medicament is an aerosolized osmolyte.

3. The apparatus of claim 1, wherein the aerosolized medicament is hypertonic saline.

4. The apparatus of claim 1, further comprising:
an aerosol preparation mechanism, the aerosol preparation mechanism configured to produce the aerosolized medicament including respirable particles having a particle size of 1-5 microns MMD.

5. The apparatus of claim 1, wherein the nasal cannula assembly is configured to deliver the aerosolized medicament to the subject over a period of at least 80 minutes.

6. The apparatus of claim 1, wherein the nasal cannula assembly is configured to deliver the aerosolized medicament to the subject over a period of at least 80 minutes, the aerosolized medicament having a particle size of 1-5 microns MMD.

7. The apparatus of claim 1, further comprising:
a heater configured to heat at least a portion of the nasal cannula assembly such that condensation of the aerosolized medicament in the nasal cannula assembly is limited.

8. The apparatus of claim 1, wherein an inner surface of the nasal cannula assembly includes a coating formulated to minimize accumulation of the aerosolized medicament.

9. The apparatus of claim 1, wherein a length from the first end portion of the nasal cannula assembly to the second end portion of the nasal cannula assembly is at least two meters.

10. The apparatus of claim 1, wherein at least a portion of the nasal cannula assembly has an inner diameter of less than five millimeters.

11. The apparatus of claim 1, wherein a delivery portion of the second end portion of the nasal cannula assembly is tapered such that it can engage at least one nostril of the subject.

12. The apparatus of claim 1, further comprising:
an aerosol preparation mechanism configured to receive a flow of air at a first port and produce the flow of aerosolized medicament, the aerosol preparation mechanism configured to convey, from a second port and to the first end portion of the nasal cannula assembly, the flow of aerosolized medicament.

13. The apparatus of claim 1, further comprising:
an aerosol preparation mechanism configured to receive a flow of air at a first port, the aerosol preparation mechanism configured to convey over a period of at least 80 minutes, from a second port and to the first end portion of the nasal cannula assembly, the flow of aerosolized medicament.

14. An apparatus, comprising:
a nasal cannula assembly having a tube portion and a face piece portion, the tube portion configured to be coupled to an aerosol preparation mechanism, the face piece portion configured to be coupled to a nostril of a subject, the nasal cannula assembly configured to receive, at the tube portion and from the aerosol preparation mechanism, an aerosolized osmolyte, the nasal cannula assembly configured to convey, over a period of at least eighty minutes and via the face piece portion, the aerosolized osmolyte to the nostril of the subject, the nasal cannula assembly configured to limit accumulation of liquid droplets therein.

15. The apparatus of claim 14, further comprising:
a heater configured to heat at least a portion of the nasal cannula assembly such that condensation of the aerosolized osmoltye in the nasal cannula assembly is limited.

16. The apparatus of claim 14, further comprising:
the aerosol preparation mechanism, the aerosol preparation mechanism configured to produce the aerosolized osmolyte including respirable particles having a particle size of 1-5 microns MMD.

17. The apparatus of claim 14, wherein a portion of the face piece portion is tapered such that it can engage the nostril of the subject.

18. The apparatus of claim 14, wherein an inner surface of the nasal cannula assembly includes a coating formulated to minimize accumulation of the aerosolized osmolyte.

19. The apparatus of claim 14, wherein the nasal cannula assembly is configured to convey the aerosolized osmolyte over a period of at least about 8 hours.

20. The apparatus of claim 14, further comprising:
a container containing the aerosolized osmolyte, the aerosolized osmolyte formulated to treat chronic obstructive pulmonary disease.

21. An apparatus, comprising:
a nasal cannula assembly having a tube portion and a face piece portion, the tube portion configured to be operably coupled to an aerosol preparation mechanism, the face piece portion configured to be removably coupled to a nostril of a subject,
the nasal cannula assembly configured to receive, at the tube portion and from the aerosol preparation mechanism, a flow of aerosolized osmolyte including respirable particles having a particle size of 1-5 microns MMD, the nasal cannula assembly configured to convey, via the face piece portion, the aerosolized osmolyte to the notstril of the subject, the nasal cannula assembly configured to limit accumulation of the aerosolized osmolyte therein.

22. The apparatus of claim 21, further comprising:
the aerosol preparation mechanism, the aerosol preparation mechanism configured to produce the aerosolized osmolyte.

23. The apparatus of claim 21, further comprising:
a heater configured to heat at least a portion of the nasal cannula assembly such that condensation of the aerosolized osmolyte in the nasal cannula assembly is limited.

24. The apparatus of claim 21, wherein the nasal cannula assembly is configured to convey the aerosolized osmolyte over a period of at least about 8 hours.

25. The apparatus of claim 21, further comprising:
the aerosol preparation mechanism, the aerosol preparation mechanism configured to receive a flow of air at a first port and produce the flow of aerosolized osmolyte, the aerosol preparation mechanism configured to convey, from a second port and to a first end of the tube portion of the nasal cannula assembly, the flow of aerosolized osmolyte.

* * * * *